(12) United States Patent
Jansson et al.

(10) Patent No.: US 11,400,426 B2
(45) Date of Patent: Aug. 2, 2022

(54) SYSTEM AND METHOD FOR PREPARATION OF A MEDICAL FLUID

(71) Applicant: Gambro Lundia AB, Lund (SE)

(72) Inventors: Olof Jansson, Vellinge (SE); Sture Hobro, Lund (SE); Lennart Jonsson, Bjarred (SE)

(73) Assignee: Gambro Lundia AB, Lund (SE)

( * ) Notice: Subject to any disclaimer, the term of this patent is extended or adjusted under 35 U.S.C. 154(b) by 949 days.

(21) Appl. No.: 16/131,555

(22) Filed: Sep. 14, 2018

(65) Prior Publication Data

US 2019/0015800 A1 Jan. 17, 2019

Related U.S. Application Data

(62) Division of application No. 14/783,937, filed as application No. PCT/EP2014/057700 on Apr. 16, 2014, now Pat. No. 10,076,735.

(30) Foreign Application Priority Data

Apr. 25, 2013 (SE) .................................. 1350515-1

(51) Int. Cl.
*B01F 15/00* (2006.01)
*B01F 15/02* (2006.01)
(Continued)

(52) U.S. Cl.
CPC ....... *B01F 35/2132* (2022.01); *A61M 1/1656* (2013.01); *A61M 1/1666* (2014.02);
(Continued)

(58) Field of Classification Search
CPC ........ B01F 15/00285; B01F 2015/0221; B01F 35/2132; B01F 35/2202; G05D 11/138
See application file for complete search history.

(56) References Cited

U.S. PATENT DOCUMENTS

| 6,635,026 B1 | 10/2003 | Bene |
| 6,793,827 B1 | 9/2004 | Bosetto et al. |

(Continued)

FOREIGN PATENT DOCUMENTS

| CA | 1183461 | 3/1985 |
| EP | 160272 | 11/1985 |

(Continued)

OTHER PUBLICATIONS

International Search Report—PCT/EP2014/057700—dated Aug. 18, 2014—3 pages.

(Continued)

*Primary Examiner* — Elizabeth Insler
(74) *Attorney, Agent, or Firm* — K&L Gates LLP (57) ABSTRACT

Systems and apparatuses for preparing a medical fluid are disclosed. In an example embodiment, a system is configured to initially control a dosing of a first concentrate, while not feeding a second concentrate, under feedback control via a concentration sensor to a first pump to feed the first concentrate. When a concentration has reached a preselected concentration level, a value for a feeding parameter for the first pump to feed the first concentrate is determined. Additionally, the system is configured to control the dosing of both the first and the second concentrates by switching the feedback control via the concentration sensor, from control of the first pump to control of a second pump to feed the second concentrate. During this time, the system controls the first pump to feed the first concentrate based on the determined value of the feeding parameter.

11 Claims, 4 Drawing Sheets

(51) Int. Cl.
    *A61M 1/16*         (2006.01)
    *B01F 35/21*        (2022.01)
    *G05D 11/13*       (2006.01)
    *B01F 35/22*        (2022.01)
    *B01F 35/71*        (2022.01)
    *B01F 35/83*        (2022.01)

(52) U.S. Cl.
    CPC ...... *B01F 35/2202* (2022.01); *B01F 35/7176* (2022.01); *B01F 35/8311* (2022.01); *G05D 11/138* (2013.01); *B01F 35/715* (2022.01)

(56) References Cited

U.S. PATENT DOCUMENTS

| | | | |
|---|---|---|---|
| 2006/0285429 A1 | 12/2006 | Kamimura et al. | |
| 2007/0279038 A1 | 12/2007 | Takada et al. | |
| 2008/0279038 A1* | 11/2008 | Bellafiore | ............ G05D 11/139 366/152.4 |

FOREIGN PATENT DOCUMENTS

| | | |
|---|---|---|
| FR | 2504817 | 11/1982 |
| WO | 2007010316 | 1/2007 |
| WO | 2008112945 | 9/2008 |
| WO | 2011162666 | 12/2011 |

OTHER PUBLICATIONS

Alquist, Marie et al., "First Clinical Experience With a New Concentrate System for Dialysis With Dry Sodium Chloride," ASAIO Journal (1998), vol. 44, pp. M592-M595—XP-000802380.
U.S. Appl. No. 14/783,937 Non-Final Rejection dated Jan. 10, 2018.

\* cited by examiner

Figure 1

PRIOR ART

SYSTEM AND METHOD FOR PREPARATION OF A MEDICAL FLUID

PRIORITY CLAIM

This application claims priority to and the benefit as a divisional of U.S. patent application Ser. No. 14/783,937, filed on Oct. 12, 2015, now U.S. Pat. No. 10,076,735, which is a National Phase of International Application No. PCT/EP2014/057700, filed on Apr. 16, 2014, which claims priority to Swedish Patent Application No. 1350515-1, filed on Apr. 25, 2013, the entire contents of each of which are incorporated herein by reference and relied upon.

TECHNICAL FIELD

The present invention relates to a system and a method for dosing of at least two concentrates into water for on-line preparation of a medical fluid. The system comprises a main line for feeding of water, a first line with a first pump for feeding of a first concentrate into the main line at a first mixing point, a second line with a second pump for feeding of a second concentrate into the main line at a second mixing point, and a main concentration sensor arranged in the main line downstream both the first and the second mixing points. The method comprises the steps of feeding water in a main line, feeding a first concentrate in a first line by a first pump into the main line at a first mixing point, feeding a second concentrate in a second line by a second pump into the main line at a second mixing point, and measuring a concentration in the main line downstream both the first and the second mixing points by a main concentration sensor.

BACKGROUND OF THE INVENTION

A number of various extracorporeal blood treatments exist. Exam-pies are hemodialysis, hemofiltration and hemodiafiltration, which all make use of a filter and are often called dialysis. Dialysis may also be performed as peritoneal dialysis, where no withdrawal of the blood takes place. Instead a so called pd-solution is kept in the abdominal cavity of the patient for specified periods of time.

A conventional filter for dialysis comprises a first and a second compartment separated by a membrane. The first compartment has an inlet and an outlet for the circulation of blood there through. The second compartment has an outlet for draining a liquid (e.g. plasma water and used dialysis liquid) and in case the treatment (as in the case of hemodialysis) requires the circulation of a treatment liquid (e.g. a dialysis liquid), the second compartment also has an inlet.

In the above treatments, blood is withdrawn from the patient, flown through the first compartment of the filter, and returned to the patient. This part is the so called extracorporeal blood circuit. In case excess water is to be withdrawn from the blood, this is done across the membrane. In hemodialysis, a dialysis liquid is simultaneously flown through the second compartment of the filter and the metabolic wastes contained in the blood migrate by diffusion over the membrane into the second compartment. In hemofiltration, a pressure difference is created across the membrane so that plasma water flows through the membrane into the second compartment. Metabolic wastes migrate by convection into the second compartment. In order to compensate for the excess loss of body fluid, the patient is simultaneously infused with a sterile substitution solution. Hemodiafiltration is a combination of hemodialysis and hemofiltration. In this treatment a dialysis liquid is flown through the second compartment and a substitution solution is infused into the patient.

The dialysis liquid is thus flown from a fluid source and into a fluid circuit, which comprises the second compartment of the filter, where the blood is treated. After having passed the second compartment of the filter, the dialysis liquid is disposed to a drain.

There are a number of ways to prepare the dialysis fluid and the replacement fluid, both called treatment fluid below. Basically, different components, often in the form of a concentrate in fluid or powder form, are to be mixed with pure water. Generally the preparation can be done according to one of two basic principles. The first one is batch preparation and the second one is on-line preparation. In batch preparation the treatment fluid is prepared before the treatment starts. All components that are needed are put into a container together with water and a mixing takes place. Thus, the concentration of the different components in relation to each other cannot be changed once the treatment has started. This document will focus on the on-line preparation.

In on-line preparation of a treatment fluid, the preparation is continuous during the session of blood treatment of a patient. The preparation typically includes feeding of water in a main line and adding the concentrates one after the other along the main line. A ready-to-use treatment fluid is delivered at the downstream end of the main line. Thus, the downstream end of the main line is the output from the fluid source mentioned above. Thus, in the case of a dialysis liquid, the downstream end of the main line is directly connectable to the upstream end of the fluid circuit. As is known in the art, the fluid source is typically part of a dialysis machine. The concentrates that are being added to the main line are typically in fluid or powder form and are being fed by one pump each. If two concentrates are needed for the dialysis liquid, one may be in fluid form and the other one may be in powder form.

If the concentrate is in fluid form, it is fed by a pump in a feeding line, which is connected to the main line at a mixing point. The concentrate is fed at a suitable feeding speed to be properly diluted when it is mixed with the water in the main line.

If the concentrate is in powder form, the continuous preparation typically includes feeding a stream of water into a container that holds a concentrate in powder form that is dissolved by the water. The water and the dissolved substance form a fluid concentrate, which is delivered from the container and which is treated in the same way as the fluid concentrate above.

Typically, more than one concentrate have to be diluted with water and mixed together to achieve a treatment fluid with all required components, each concentrate having its own pump.

Definitions

In the following the term medical fluid is used for both a dialysis fluid and a replacement fluid in various extracorporeal blood treatments. It is also used for a fluid which will become a ready-to-use dialysis fluid or replacement fluid with the addition of further components. The term medical fluid is also used for a pd-solution for peritoneal dialysis.

SUMMARY OF THE INVENTION

It is an object of the present invention to provide an alternative system and method for dosing of at least two concentrates into water for on-line preparation of a medical fluid. In particular it is an object that the system is configured to be part of a dialysis machine or to be connectable to a dialysis machine. In the case of peritoneal dialysis, the medical fluid may be delivered directly to the patient or may be delivered into bags connectable or connected to a cycler for e.g. nocturnal use or later use.

All of the disclosed embodiments may not fulfil all of the disclosed objectives.

Hence a system is provided, which is configured to initially control the dosing of the first concentrate, while not feeding any of the second concentrate, under feedback control from the main concentration sensor to the first pump for feeding of the first concentrate, such that when the concentration measured by the main concentration sensor has reached a first preselected concentration level, a value for a feeding parameter for the first pump for feeding of the first concentrate is determined. After the determination of the value for the feeding parameter, the system is configured to control the dosing of both the first and the second concentrate during the continued on-line preparation of the medical fluid, such that the feedback control from the main concentration sensor is moved, from control of the first pump for feeding of the first concentrate, to control of the second pump for feeding of the second concentrate, and that the value for the feeding parameter is used for control of the first pump for feeding of the first concentrate.

Hence a method is provided having the steps of initially, while not feeding any of the second concentrate, controlling the dosing of the first concentrate, under feedback control from the main concentration sensor to the first pump for feeding of the first concentrate, such that when the concentration measured by the main concentration sensor has reached a first preselected concentration level, a value for a feeding parameter for the first pump for feeding of the first concentrate is determined. After the determination of the value for the feeding parameter, controlling the dosing of both the first and the second concentrate during the continued on-line preparation of the medical fluid, by moving the feedback control from the main concentration sensor, from control of the first pump for feeding of the first concentrate, into control of the second pump for feeding of the second concentrate, and by using the value for the feeding parameter for control of the first pump for feeding of the first concentrate.

The system and method of the invention provides the advantage that less components are needed compared to many traditional dialysis moni-tors, especially so for the expensive concentration sensors enabling production of a dialysis monitor at a lower cost.

Another advantage is that the system and the method according to the invention give the possibility of achieving a more accurate dosing.

The system may be such that the feedback control from the main concentration sensor, when controlling the second pump for feeding of the second concentrate, is such that a second preselected concentration level is maintained or that a predetermined pro-filing curve for the concentration is followed.

The feeding parameter of the system may be a flow rate of the first concentrate in the first line.

The feeding parameter of the system may be a ratio between a flow of the first concentrate in the first line and a fluid flow in the main line.

The feeding parameter of the system may be a ratio between a flow of the first concentrate in the first line and a fluid flow in the main line downstream both the first and the second mixing points.

In one embodiment the system may comprise one single concentration sensor, the main concentration sensor, for dosing of two concentrates into water for on-line preparation of a medical fluid.

In another embodiment the system may comprise a secondary concentration sensor, arranged between the first mixing point and the second mixing point, providing an output which constitutes the feeding parameter for control of the first pump for feeding of the first concentrate.

The method may be such that the feedback control from the main concentration sensor, when controlling the second pump for feeding of the second concentrate, is such that a second preselected concentration level is maintained or that a predetermined profiling curve for the concentration is followed.

The feeding parameter of the method may be a flow rate of the first concentrate in the first line.

The feeding parameter of the method may be a ratio between a flow of the first concentrate in the first line and a fluid flow in the main line.

The feeding parameter of the method may be a ratio between a flow of the first concentrate in the first line and a fluid flow in the main line downstream both the first and the second mixing points.

In one embodiment of the method one single concentration sensor, the main concentration sensor, is used for dosing of two concentrates into water for on-line preparation of a medical fluid.

In another embodiment of the method a secondary concentration sensor being arranged between the first mixing point and the second mixing point, having an output which constitutes the feeding parameter for control of the first pump for feeding of the first concentrate.

Still other objectives, features, aspects and advantages of the invention will appear from the following detailed description, from the attached claims as well as from the drawings.

BRIEF DESCRIPTION OF THE DRAWINGS

Embodiments of the invention will now be described, by way of example, with reference to the accompanying schematic drawings, in which.

DETAILED DESCRIPTION OF THE INVENTION

Figure 1:
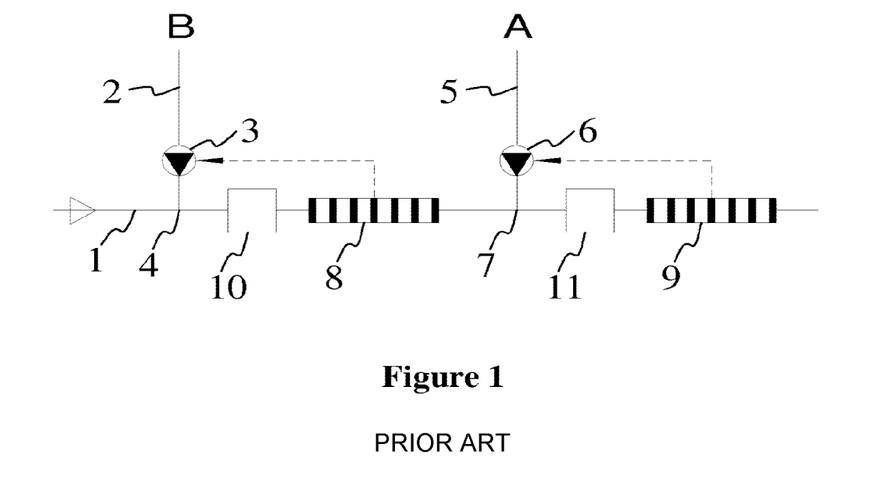
FIG. 1 is a schematic view showing the principle of a system for dosing of two concentrates into water for on-line preparation of a medical fluid according to the prior art.

FIG. 1 shows the basic principle of preparation of a treatment fluid according to the prior art. It includes feeding of water in a main line and adding the concentrates one after the other along the main line. The concentrates may be in fluid form delivered from e.g. a canister, or may be prepared from a powder in a cartridge. A ready-to-use treatment fluid is delivered at the downstream end of the main line. Thus, the system includes a main line 1 for feeding of water (the source of water being at the upstream end of the main line and is not shown), a first line 2 with a first pump 3 for feeding of a first concentrate into the main line at a first mixing point 4. The system also includes a second line 5 with a second pump 6 for feeding of a second concentrate into the main line at a second mixing point 7. A first conductivity sensor 8 is arranged in the main line between the first mixing point 4 and the second mixing point 7, and a second conductivity sensor 9 is arranged in the main line downstream both the first and the second mixing points.

For the preparation of a treatment fluid, typically one A-concentrate and one B-concentrate are needed. The A-concentrate is an acidic liquid with a number of electrolytes, among others often NaCl (sodium chloride), and the B-concentrate comprises $NaHCO_3$ (sodium bicarbonate) dissolved in water.

It is known that the ions in the concentrates contribute to the conductivity of the prepared fluid. It is also known that different ions give a specific contribution to the conductivity. This means that a fluid with a certain composition of ions has a corresponding certain conductivity that can be calculated. This conductivity may be used for dosing of a specific amount of a concentrate with a conductivity sensor. For a dialysis treatment, the sodium and bicarbonate concentrations are often specified individually for each patient by the doctor. The sodium and bicarbonate concentrations may also be profiled over time.

The first conductivity sensor 8 has a feedback control to the first pump 3 for feeding of the first concentrate. This feedback control is showed with a dashed line in FIG. 1. The feedback control has a preselected conductivity level as a desired level, which has been calculated based upon the composition of the concentrate and upon the desired levels, i.e. concentrations, of certain components in the ready-to-use treatment fluid. The calculation has been done before the treatment starts, e.g. already during the manufacturing of the dialysis machine. However the composition of the ready-to-use treatment fluid may be adjusted before or during the treatment by an attendant like a nurse. In such a case the machine recalculates the preselected conductivity level that is to be the desired level.

The second conductivity sensor 9 has a feedback control to the second pump 6 for feeding of the second concentrate. This feedback control is showed with a dashed line in FIG. 1. This feedback control has another preselected conductivity level as a desired level, which also has been calculated based upon the composition of the concentrate and upon the desired levels, i.e. concentrations, of certain components in the ready-to-use treatment fluid. Also this calculation has been done before the treatment starts, and the ready-to-use treatment fluid may be adjusted and the preselected conductivity level recalculated as above.

It is known to add the A-concentrate before the B-concentrate along the main line in the flow direction, known as A+B, such that the A-concentrate is the first concentrate in the above description. It is also known to add the B-concentrate before the A-concentrate along the main line, known as B+A, such that the B-concentrate is the first concentrate in the above description. The B+A version is shown in FIG. 1.

The system in FIG. 1 has a first mixing chamber 10 arranged in the main line 1 after the first mixing point 4 and before the first conductivity sensor 8. This system also has a second mixing chamber 11 arranged in the main line 1 after the second mixing point 7 and before the second conductivity sensor 9. A mixing chamber decreases possible main flow concentration variations created by the pump pumping the concentrate to the mixing point upstream the mixing chamber.

Figure 2:
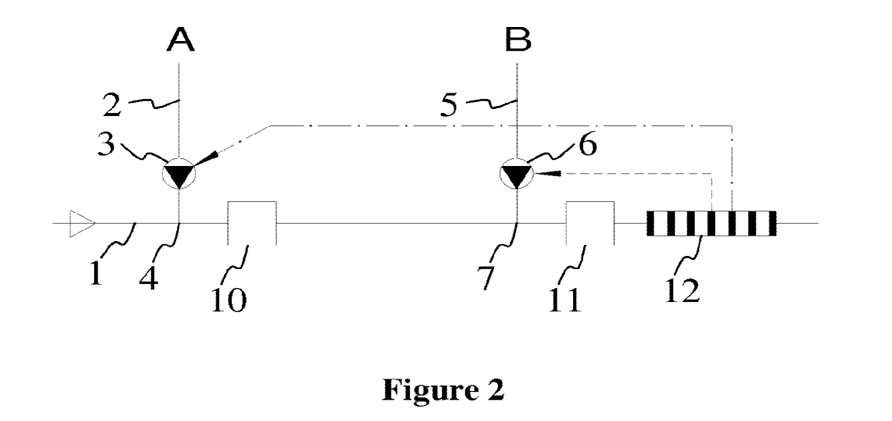
FIG. 2 is a schematic view showing the principle of a system for dosing of two concentrates into water for on-line preparation of a medical fluid according to one embodiment of the invention.

With reference to FIG. 2, one embodiment of the inventive system for preparation of a medical fluid is shown. Some parts are the same as for the system in FIG. 1, and have been given the same reference numbers.

The system according to this embodiment of the invention includes a main line 1 for feeding of water, (the source of water being at the upstream end of the main line and is not shown), a first line 2 with a first pump 3 for feeding of a first concentrate into the main line at a first mixing point 4. The system also includes a second line 5 with a second pump 6 for feeding of a second concentrate into the main line at a second mixing point 7. A main concentration sensor 12 is arranged in the main line downstream both the first and the second mixing points 4, 7.

The main concentration sensor may be of the type conductivity sensor or ion selective sensor. It may also be a detector of the type measuring e.g. density, optical refraction or optical polarisation angle.

The system is configured to have a feedback control from the main concentration sensor 12, which is initially controlling the first pump 3 for feeding of the first concentrate. This feedback control is showed with a dash dotted line in FIG. 2. This could be called the start-up phase or the initial phase of the on-line preparation. At a certain point in time the feedback control is moved from controlling the first pump 3 for feeding of the first concentrate, into controlling the second pump 6 for feeding of the second concentrate, as will be described below. This feedback control is showed with a dashed line in FIG. 2. This could be called the continued phase of the on-line preparation. In this embodiment the first line 2 is shown upstream of the second line 5, however the second line 5 could be arranged upstream of the first line 2.

Initially, only the first concentrate is fed by the first pump 3, while there is no feeding of the second concentrate by the second pump 6. The main concentration sensor 12 measures the concentration of the fluid in the main line 1, i.e. of the first concentrate mixed with water. The measurement takes place continuously or repeatedly at suitable sampling intervals, as is known in the art. The feedback control from the main concentration sensor 12 to the first pump 3 for feeding of the first concentrate is such that when the concentration measured by the main concentration sensor has reached a first preselected concentration level, a value for a feeding parameter for the first pump 3 for feeding of the first concentrate is determined.

The system may be provided with a memory of the kind known in the art, for storing of the value for the feeding parameter. The value for the feeding parameter may be retrieved from the memory when needed for the control of the first pump 3 for feeding of the first concentrate.

After the determination of the value for the feeding parameter, the system is configured to control the dosing of both the first and the second concentrate during the continued on-line preparation of the medical fluid. The value for the feeding parameter is used for control of the first pump 3 for feeding of the first concentrate. The feeding of the second concentrate by the second pump 6 is started and the feedback control from the main concentration sensor 12 is moved from control of the first pump 3 for feeding of the first concentrate, to control of the second pump 6 for feeding of the second concentrate.

The feeding parameter may be the flow rate of the first concentrate in the first line 2. As an alternative the feeding parameter may be the pump speed of the first pump 3. As yet another alternative the feeding parameter may be a feed voltage to drive the first pump. A still further alternative is that the feeding parameter is a ratio between the flow of the first concentrate in the first line 2 and the fluid flow in the main line 1. The fluid flow in the main line 1 may be determined downstream both the first and the second mixing points 4, 7, or alternatively between the mixing points 4, 7, or even upstream the first mixing point 4. The control of the first pump 3 by the feeding parameter is an open loop control without feedback from the main concentration sensor 12.

In one embodiment the first pump 3 is a volumetric pump. It is known to the man skilled in the art that in the case of a volumetric pump a constant flow rate could be achieved if the pump speed or the feed voltage to the pump is kept constant, in some cases with the need of consideration of the load on the pump.

In many dialysis machines the flow rate of the fluid in the main line 1 downstream both the first and the second mixing points 4, 7, called Q, is kept at a constant rate of e.g. 500 ml/min. This is e.g. done by a pump in combination with a throttle valve. When only the first pump 3 is feeding its concentrate, this fluid flow rate Q is the sum of the fluid flow rates of the first concentrate and water. When also the second pump 6 starts feeding its concentrate, the fluid flow rate Q is the sum of the fluid flow rates of the first concentrate, the second concentrate and water. Thus, if the fluid flow rate Q is to be kept constant also during the continued phase of the on-line preparation, when the second pump 6 has started feeding its concentrate, the fluid flow rate of water has to be reduced.

The feedback control from the main concentration sensor 12, when controlling the second pump 6 for feeding of the second concentrate, is such that a second preselected concentration level is maintained or a predetermined profiling curve for the concentration is followed.

The system shown in FIG. 2 is of the type A+B. However, it is fully possible to have the system as a B+A instead, i.e. both orders of the concentrates as A+B or B+A in the flow direction are possible.

If both concentrates are stable, i.e. if both concentrates are in liquid form, it does not matter which concentrate is denoted the first concentrate and which is denoted the second concentrate.

If however, one of the concentrates is in powder form, the concentration may vary over time due to e.g. temperature changes. Thus, the preferred version in the case of a stable first concentrate in liquid form and a more un-stable second concentrate in powder form, is to determine a feeding parameter for the pump pumping the first concentrate, and having the feedback control from the main concentration sensor 12, when the feeding parameter has been determined, to control the pump pumping the second concentrate.

This is typically the case if the A-concentrate is in liquid form either from a rigid or soft container e.g. from a canister or as a centrally delivered concentrate in a dialysis clinic, and the B-concentrate is prepared from a powder in a cartridge on the dialysis machine.

In some cases it might become necessary to rescale the value of the feeding parameter. This is just a recalculation of the value, and no new measurement by the main concentration sensor 12 is made. If e.g. the fluid flow rate in the main line 1 downstream both the first and the second mixing points 4, 7, is changed from 500 ml/min to 700 ml/min, the second pump 6 for feeding of the second concentrate will automatically adjust to the new fluid flow rate due to the feedback control from the main concentration sensor 12. The value for the feeding parameter was however determined in relation to the initial fluid flow rate of, in this example 500 ml/min. A rescaling in the form of a recalculation will adjust the value for the feeding parameter to the new fluid flow rate of 700 ml/min i.e. a larger amount of the first concentrate will be added per time unit to the medical fluid. After this rescaling the relation of the components in relation to each other in the prepared medical fluid is again correct.

A rescaling might also be needed if the nurse sets an amended desired value for e.g. the sodium or bicarbonate concentration. The pump pumping the B-concentrate will adjust automatically to the new desired concentration value due to the feedback control from the main concentration sensor 12, while the value for the feeding parameter will be recalculated as a new value in relation to the new desired concentration value. Profiling in accordance with a predetermined profiling curve for the concentration is analogous.

The system according to the embodiment in FIG. 2 may be provided with a first mixing chamber 10 and/or a second mixing chamber 11, but these are optional.

Since concentration sensors are expensive, one advantage with the embodiment shown in FIG. 2 is that it has only one single concentration sensor, which makes it possible to produce this embodiment at a lower cost compared to many traditional dialysis machines.

The embodiment shown in FIG. 2 may be provided with a secondary concentration sensor (not shown) arranged between the first mixing point 4 and the second mixing point 7. This secondary concentration sensor may be of the same type as the main concentration sensor 12 and may be configured to measure the concentration of the first concentrate mixed with water. The concentration measurement by the secondary concentration sensor may be used for protective purpose e.g. to issue an alert to an attendant, issue an alarm, and/or bypass the dialysis filter and potentially take other measures when the output is outside given limits.

As an alternative, the secondary concentration sensor may be configured to measure the concentration of the first concentrate mixed with water at the same time as the main concentration sensor during the initial phase. When the concentration measured by the main concentration sensor 12 has reached the first preselected concentration level, the concentration value as measured by the secondary concentration sensor is determined as the value of the feeding parameter for control of the first pump for feeding of the first concentrate. Thus, the feeding parameter in this case is the concentration as measured by the secondary concentration sensor, used for feedback control of the first pump 3.

This embodiment, when the concentration value as measured by the secondary concentration sensor is determined as the value of the feeding parameter, have the placing of the secondary concentration sensor in common with the placing of the first concentration sensor 8 in the system in FIG. 1. However there are fundamental differences between these two systems. The preselected concentration level for the secondary concentration sensor is actually measured, and the point in time when this measurement is made is determined by the main concentration sensor 12. This is not the case for the first concentration sensor 8 in the system in FIG. 1, in which the preselected concentration level is instead calculated. The main concentration sensor 12 is configured to initially, under feedback control, control the dosing of the first concentrate, and then under feedback control, control the dosing of the second concentrate. This moving of the feedback control has no correspondence in the system in FIG. 1.

Figure 3:
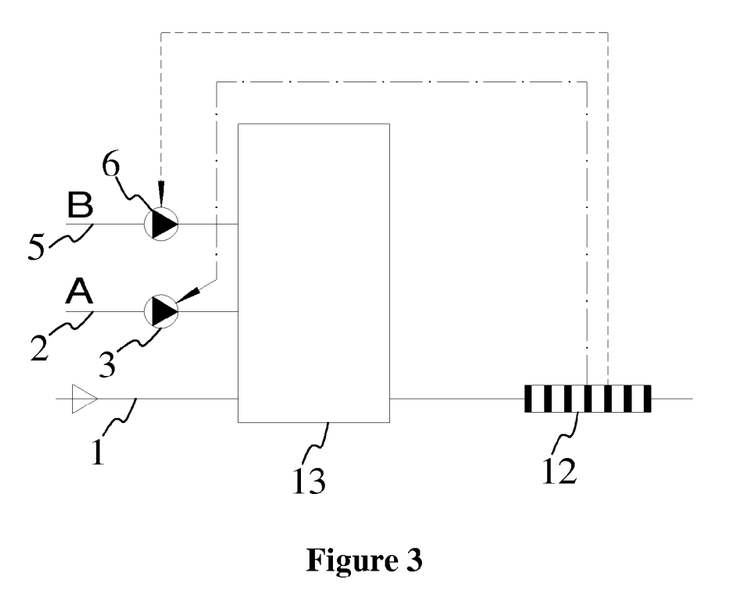
FIG. 3 is a schematic view showing the principle of a system for dosing of two concentrates into water for on-line preparation of a medical fluid according to another embodiment of the invention.

FIG. 3 shows another embodiment of the invention, which is a modification of the embodiment shown in FIG. 2. The system according to this embodiment of the invention includes a main line 1 for feeding of water, (the source of water being at the upstream end of the main line and is not shown), which main line 1 is provided with a mixing chamber 13 and a main concentration sensor 12, arranged in the main line downstream the mixing chamber 13. The mixing chamber 13 corresponds to the second mixing chamber 11 in the embodiment shown in FIG. 2.

The system also includes a first line 2 with a first pump 3, which first line 2 discharges into the mixing chamber 13, for feeding of a first concentrate into the mixing chamber 13. The system furthermore includes a second line 5 with a second pump 6, which second line 5 discharges into the mixing chamber 13, for feeding of a second concentrate into the mixing chamber 13.

This embodiment is similar to the embodiment in FIG. 2, with the first mixing chamber 10 removed and the second mixing chamber 11 present, now denoted 13. From making this comparison it is clear that both the first line 2 and the second line 5 could discharge in the main line 1 at mixing points therein. From this it is also clear that the main concentration sensor 12 is arranged in the main line downstream both the first and the second mixing points. To have as good conditions as possible for the measurement by the main concentration sensor 12, the mixing chamber 13 should be arranged upstream the main concentration sensor 12.

The main concentration sensor may be of the same type as mentioned for the embodiment shown in FIG. 2.

The system is configured to have a feedback control from the main concentration sensor 12, in the same way as is described for the embodiment shown in FIG. 2. The initial feedback control of the first pump 3 for feeding of the first concentrate is showed with a dash dotted line in FIG. 3, denoting the initial phase of the on-line preparation. The feedback control for controlling the second pump 6 for feeding of the second concentrate is showed with a dashed line in FIG. 3, denoting the continued phase of the on-line preparation.

As in the embodiment shown in FIG. 2, the feeding parameter may be the flow rate of the first concentrate in the first line 2, the pump speed of the first pump 3, or a feed voltage to drive the first pump. The feeding parameter may also be a ratio between the flow of the first concentrate in the first line 2 and the fluid flow in the main line 1. The fluid flow in the main line 1 may be determined downstream both the first and the second mixing points, i.e. in this case after the mixing chamber 13. Alternatively in this embodiment it may be determined upstream the mixing chamber 13.

Figure 4:
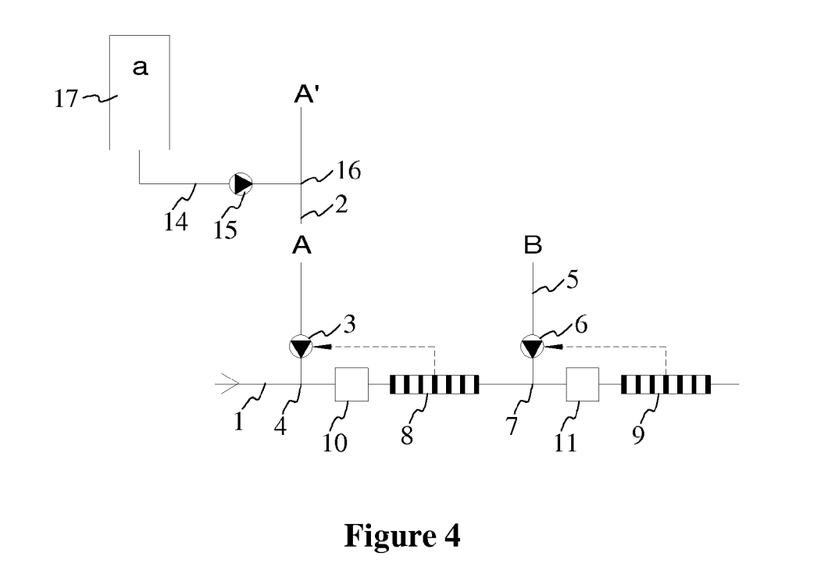
FIG. 4 is a schematic view showing a system according to the prior art similar to the system shown in FIG. 1.

Reference is now made to FIG. 4, which is a schematic view showing a system according to the prior art similar to the system shown in FIG. 1. Some parts are the same as for the system in FIG. 1, and have been given the same reference numbers. These parts will not be described again with reference to FIG. 4.

The system shown in FIG. 4 is an A+B system, in which the A-concentrate has been divided in two parts, one part denoted A' consisting of the NaCl (sodium chloride) as a concentrate in powder form, and another part denoted "a" consisting of a number of electrolytes as a concentrate in liquid form. This system could be said to dose three concentrates into water for on-line preparation of a treatment fluid.

The first concentrate in the system shown in FIG. 4 is A', which is prepared from a NaCl (sodium chloride) concentrate in powder form in a cartridge. This system also has a third line 14 with a third pump 15 for feeding of a third concentrate "a" into the first line 2 at a third mixing point 16. The source 17 for the third concentrate is in many cases a bag and the third concentrate is a concentrate in liquid form consisting of a number of electrolytes.

The third concentrate is dosed volumetrically, i.e. a fixed volume is added per time unit. This volume is very small compared to the volumes of the first and the second concentrates.

At start up of the system the third pump 15 for feeding of the third concentrate "a" is started at a fixed flow rate. The first pump 3 is started and has a feedback control from the first conductivity sensor 8. This feedback control has a first preselected conductivity level as the desired level. The conductivity sensed by the first conductivity sensor 8 is thus the sum of the conductivity contribution from the first concentrate A' and the conductivity contribution from the third concentrate "a". At the same time the second pump 6 for feeding of the second concentrate is started and has a feedback control from the second conductivity sensor 9. This feedback control has a second preselected conductivity level as the desired level.

Figure 5:
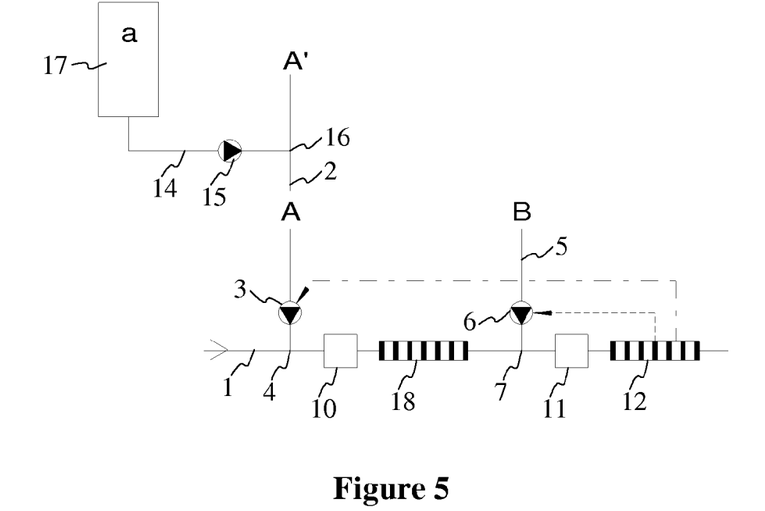
FIG. 5 is a schematic view showing the principle of a system for dosing of three concentrates into water for on-line preparation of a medical fluid according to yet another embodiment of the invention.

Reference is now made to FIG. 5, which is a schematic view showing the principle of a system for dosing of three concentrates into water for on-line preparation of a medical fluid according to yet another embodiment of the invention. Some parts are the same as for the systems in FIGS. 2 and 4, and have been given the same reference numbers. The basic inventive principle is the same as for the system shown in FIG. 2. These parts will not be described again with reference to FIG. 5.

The system shown in FIG. 5 is an A+B system, in which the A-concentrate has been divided in two parts, one part, called A', consisting of the NaCl (sodium chloride) as a concentrate in powder form, a liquid concentrate from a rigid or soft container e.g. from a canister, or as a centrally delivered concentrate in liquid form in a dialysis clinic and another part, called "a" consisting of a number of electrolytes as a concentrate in liquid form. This system doses three concentrates into water for on-line preparation of a medical fluid.

The first concentrate in the system shown in FIG. 5 is A', which is prepared from a NaCl (sodium chloride) concentrate in powder form in a cartridge, a liquid concentrate from a rigid or soft container e.g. from a canister, or is a centrally delivered concentrate in liquid form in a dialysis clinic. This system also has a third line 14 with a third pump 15 for feeding of a third concentrate, called "a", into the first line 2 at a third mixing point 16. The source 17 for the third concentrate may be e.g. a bag or a small container, and the third concentrate is a concentrate in liquid form comprising a number of electrolytes.

The third concentrate is dosed volumetrically, i.e. a fixed volume is added per time unit. This volume is very small compared to the volumes of the first and the second concentrates, but does contribute to the conductivity of the medical solution. At start up of the system the third pump 15 for feeding of the third concentrate "a" is started at a fixed flow rate. The first pump 3 is started at the same time as the third pump 15 or shortly before or shortly after.

The system shown in FIG. 5 is provided with a secondary concentration sensor 18 arranged between the first mixing point 4 and the second mixing point 7. The system is configured to have a feedback control from the main concentration sensor 12, in the same way as is described for the embodiment shown in FIG. 2. The initial feedback control of the first pump 3 for feeding of the first concentrate, together with a fixed volume of the third concentrate dosed volumetrically as described above, is showed with a dash dotted line in FIG. 5, denoting the initial phase of the on-line preparation. The feedback control for controlling the second pump 6 for feeding of the second concentrate is showed with a dashed line in FIG. 5, denoting the continued phase of the on-line preparation.

It is also possible to determine the value for the feeding parameter for the first pump 3 before the third pump 15 for feeding of the third concentrate "a" is started at a fixed flow rate. Once the third pump 15 has been started and the value for the feeding parameter has been determined, the second pump 6 for feeding of the second concentrate may be started and the continued phase of the on-line preparation may proceed.

The secondary concentration sensor 18 may be of the same type as the main concentration sensor 12. It may be configured to measure the concentration of the first concentrate mixed with water, with or without a fixed volume of the third concentrate dosed volumetrically, at the same time as the main concentration sensor 12 during the initial phase. When the concentration measured by the main concentration sensor 12 has reached the first preselected concentration level, the concentration value as measured by the secondary concentration sensor 18 is determined as the value of the feeding parameter for control of the first pump for feeding of the first concentrate together with a fixed volume of the third concentrate dosed volumetrically as described above. Thus, the feeding parameter in this case is the concentration as measured by the secondary concentration sensor 18, used for feedback control of the first pump 3.

Also this embodiment, when the concentration value as measured by the secondary concentration sensor is determined as the value of the feeding parameter, have the placing of the secondary concentration sensor in common with the placing of the first concentration sensor 8 in the system in FIG. 4. However the same fundamental differences are present between this embodiment and the system in FIG. 4 as between the embodiment shown in FIG. 2 and the system in FIG. 1, as explained above.

The system shown in FIG. 5 is of the type A+B. However, it is fully possible to have the system as a B+A instead, i.e. both orders of the concentrates as A+B or B+A in the flow direction are possible. The above described system and method for dosing according to FIG. 5 are possible where both A' and B are concentrates in powder form, i.e. the concentrations may vary over time due to e.g. temperature changes.

However, if the A'-concentrate is a liquid concentrate from a rigid or soft container e.g. from a canister, or a centrally delivered concentrate in liquid form in a dialysis clinic it can be considered as stable. In such a case, as in the embodiment shown in FIG. 2, the feeding parameter may instead be the flow rate of the first concentrate in the first line 2 after the third mixing point 16, the pump speed of the first pump 3, or a feed voltage to drive the first pump. The feeding parameter may also be a ratio between the flow of the first concentrate in the first line 2 and the fluid flow in the main line 1. The fluid flow in the main line 1 may be determined downstream both the first and the second mixing points 4, 7, or alternatively between the mixing points 4, 7, or even upstream the first mixing point 4. In these cases the concentration measurement by the secondary concentration sensor 18 may be used for protective purpose e.g. to issue an alert to an attendant, issue an alarm, and/or bypass the dialysis filter and potentially take other measures when the output is outside given limits. Thus, the secondary concentration sensor 18 is not mandatory for dosing purpose.

As in the system shown in FIG. 2, the mixing chambers 10, 11 are optional.

Figure 6:
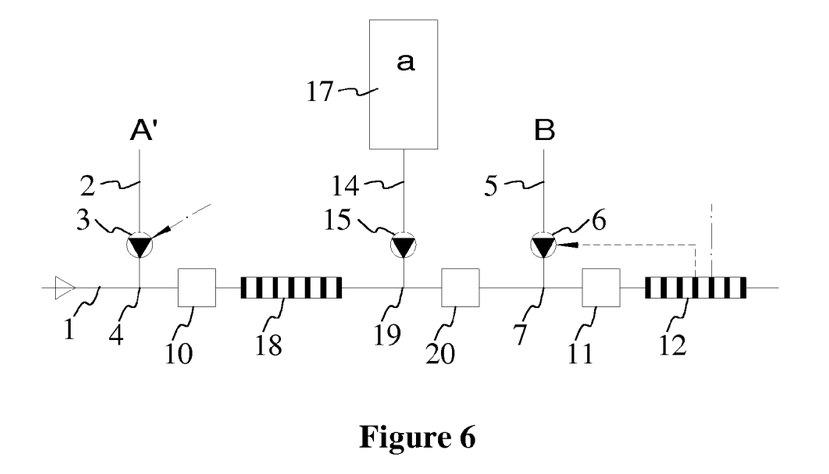
FIG. 6 is a schematic view showing the principle of a system for dosing of three concentrates into water for on-line preparation of a medical fluid according to still another embodiment of the invention.

Reference is now made to FIG. 6, which is a schematic view showing the principle of a system for dosing of three concentrates into water for on-line preparation of a medical fluid according to still another embodiment of the invention. The embodiment shown in FIG. 6 is an alternative to the embodiment shown in FIG. 5. Some parts are the same as for the systems in FIGS. 2 and 5, and have been given the same reference numbers. The basic inventive principle is the same as for the system shown in FIG. 2. These parts will not be described again with reference to FIG. 6.

The system shown in FIG. 6 is an A'+a+B system, in which A' is a NaCl-concentrate prepared as in the system shown in FIG. 5. This system also has a third line 14 with a third pump 15 for feeding of a third concentrate into the main line 1 at a fourth mixing point 19. The fourth mixing point is arranged downstream the first mixing point 4 and upstream the second mixing point 7. The source 17 for the third concentrate and the third concentrate "a" are as in the system shown in FIG. 5.

The third concentrate is dosed volumetrically, i.e. a fixed volume is added per time unit. This volume is very small compared to the volumes of the first and the second concentrates, but does contribute to the conductivity of the medical solution.

The system shown in FIG. 6 is provided with a secondary concentration sensor 18 arranged between the first mixing point 4 and the second mixing point 7 and upstream the fourth mixing point 19. The system is configured to have a feedback control from the main concentration sensor 12, in the same way as is described for the embodiment shown in FIG. 2. In this embodiment the first pump 3 is started and the value for its feeding parameter is determined before the third pump 15 for feeding of the third concentrate "a" is started at a fixed flow rate. The initial feedback control of the first pump 3 for feeding of the first concentrate is showed with a dash dotted line in FIG. 6, denoting the initial phase of the on-line preparation. The feedback control for controlling the second pump 6 for feeding of the second concentrate is showed with a dashed line in FIG. 6, denoting the continued phase of the on-line preparation.

It is also possible to start the third pump 15 for feeding of the third concentrate "a" at a fixed flow rate before the value for the feeding parameter for the first pump 3 is determined. In such a case it does not matter which of the first pump 3 and the third pump 15 is started first. They are both feeding their respective concentrate when the value for the feeding parameter for the first pump 3 is determined.

Once the third pump 15 has been started and the value for the feeding parameter has been determined, the second pump 6 for feeding of the second concentrate may be started and the continued phase of the on-line preparation may proceed.

The secondary concentration sensor 18 may be of the same type as the main concentration sensor 12. It may be configured to measure the concentration of the first concentrate, mixed with water, at the same time as the main concentration sensor 12 during the initial phase. When the concentration measured by the main concentration sensor 12 has reached the first preselected concentration level, the concentration value as measured by the secondary concentration sensor 18 is determined as the value of the feeding parameter for control of the first pump for feeding of the first concentrate. Thus, the feeding parameter in this case is the concentration as measured by the secondary concentration sensor 18, used for feedback control of the first pump 3.

Also this embodiment, when the concentration value as measured by the secondary concentration sensor is determined as the value of the feeding parameter, have the placing of the secondary concentration sensor in common with the placing of the first concentration sensor 8 in the system in FIG. 4. However the same fundamental differences are present between this embodiment and the system in FIG. 4 as between the embodiment shown in FIG. 2 and the system in FIG. 1, as explained above.

The system shown in FIG. 6 is of the type A'+a+B. However, it is fully possible to have the system as A'+B+a, B+a+A', B+A'+a, a+B+A' or a+A'+B instead as long as the main concentration sensor is downstream all mixing points. The above described system and method for dosing according to FIG. 6 are possible where both A' and B are concentrates in powder form, i.e. the concentrations may vary over time due to e.g. temperature changes.

However, if the A'-concentrate is a concentrate in liquid form from a rigid or soft container e.g. from a canister, or a centrally delivered concentrate in liquid form in a dialysis clinic it can be considered as stable. In such a case, as in the embodiment shown in FIG. 2, the feeding parameter may instead be the flow rate of the first concentrate in the first line 2, the pump speed of the first pump 3, or a feed voltage to drive the first pump. The feeding parameter may also be a ratio between the flow of the first concentrate in the first line 2 and the fluid flow in the main line 1. The fluid flow in the main line 1 may be determined downstream both the first and the second mixing points 4, 7, or alternatively between the mixing points 4, 7, upstream or downstream the fourth mixing point 19, or even upstream the first mixing point 4. In these cases the concentration measurement by the secondary concentration sensor 18 may be used for protective purpose as described above. Thus, the secondary concentration sensor 18 is not mandatory for dosing purpose.

As in the system shown in FIG. 2, the mixing chambers 10, 11 are optional. A third mixing chamber 20 is shown between the fourth mixing point 19 and the second mixing point 7 in FIG. 6. Also this mixing chamber is optional.

Figure 7:
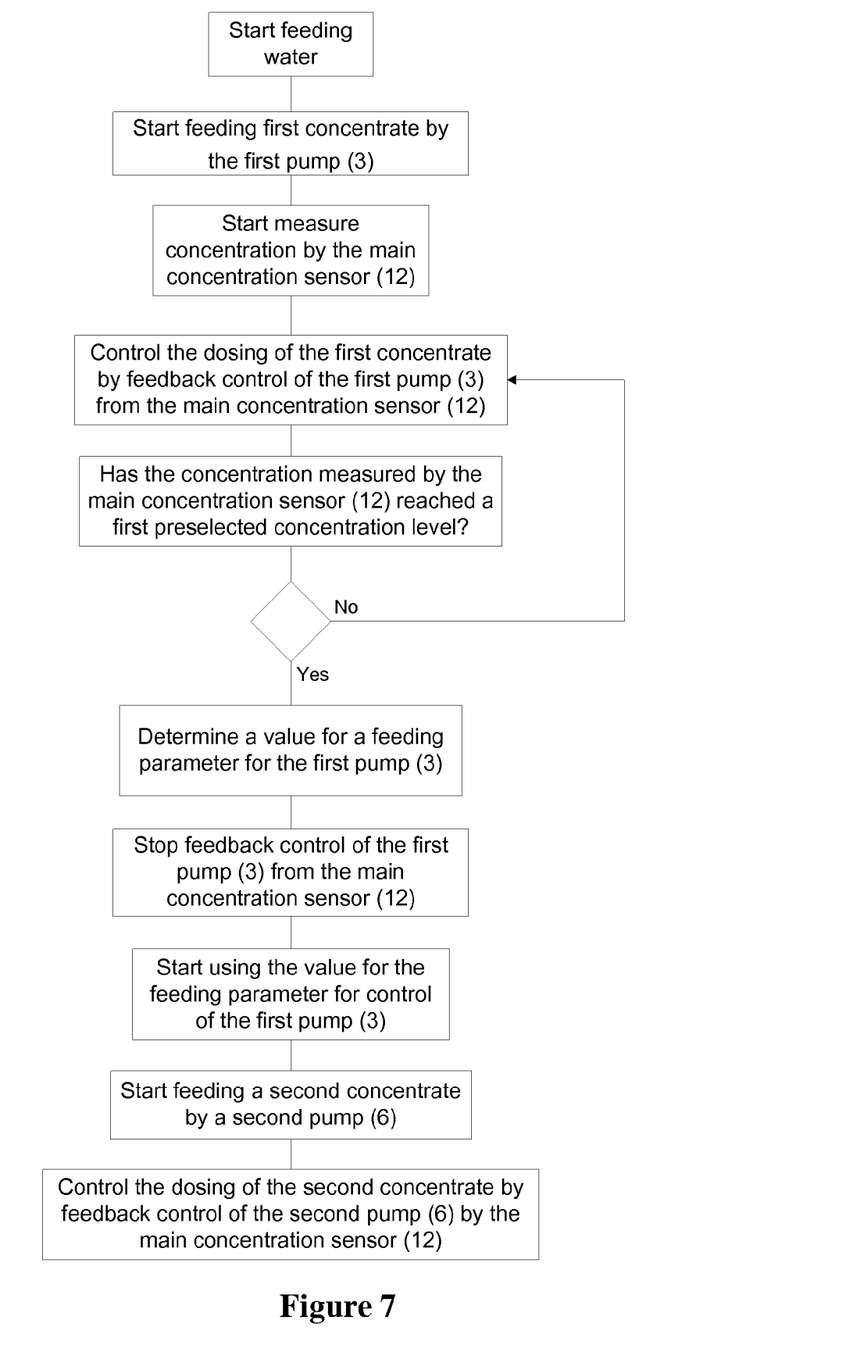
FIG. 7 is a flow chart showing the principle of a system for dosing of two concentrates into water for on-line preparation of a medical fluid according to the method of the invention.

FIG. 7 is a flow chart showing the principle of a system for dosing of two concentrates into water for on-line preparation of a medical fluid according to the method of the invention. In the flow chart the method has been divided into a number of steps. However it is to be noted that many of these steps occur more or less at the same time. As soon as the value for the feeding parameter has been determined, the system moves the feedback control from the first pump 3 to the second pump 6. Of course the second pump 6 has to be started before it can be controlled. Thus, the step "Start feeding the second concentrate by the second pump (6)" may come immediately after the step "Determine a value for a feeding parameter for the first pump (3)".

It should be understood that various changes and modifications to the presently preferred embodiments described herein will be apparent to those skilled in the art. Such changes and modifications can be made without departing from the scope of the present invention and without diminishing its attendant advantages. It is therefore intended that such changes and modifications be covered by the appended claims.

The invention is claimed as follows:

1. A dialysis apparatus having on-line preparation of a medical fluid, the apparatus comprising:
   a main line configured to receive a fluid for mixing with at least two concentrates to form the medical fluid;
   a first line operable with a first pump to feed a first concentrate into the main line at a first mixing point;
   a second line operable with a second pump to feed a second concentrate into the main line at a second mixing point;
   a concentration sensor arranged in the main line downstream of both the first and the second mixing points;
   a memory for storing a value of a feeding parameter; and
   a controller communicatively coupled to the memory and configured to
      (i) initially control the dosing of the first concentrate, while not feeding the second concentrate, by adjusting a value of a feeding parameter for operating the first pump to feed the first concentrate, such that when a concentration measured by the concentration sensor has reached a first preselected concentration level, a current value for the feeding parameter for the first pump to feed the first concentrate is stored to the memory,
      (ii) after (i), cause the current value for the feeding parameter to be accessed from the memory for controlling the first pump to control dosing of the first concentrate, and
      (iii) while performing (ii), control dosing of the second concentrate by using the concentration measured by the concentration sensor for operating the second pump to feed the second concentrate.

2. The apparatus of claim 1, wherein the fluid for mixing includes water.

3. The apparatus of claim 1, wherein the main line is configured to receive the fluid from at least one of an on-line source or a container.

4. The apparatus of claim 1, wherein the medical fluid is a dialysis fluid or a replacement fluid.

5. The apparatus of claim 1, wherein at least one of the first pump or the second pump is a volumetric pump.

6. The apparatus of claim 1, further comprising:
   a first mixing chamber located at the first mixing point for mixing the fluid with the first concentrate; and
   a second mixing chamber located at the second mixing point for mixing a mixture of the fluid and the first concentrate with the second concentrate.

7. The apparatus of claim 1, wherein the controller, when controlling the second pump to feed the second concentrate, controls the second pump such that (i) a second preselected concentration level is maintained or (ii) a predetermined profiling curve for the concentration is followed.

8. The apparatus of claim 1, wherein the feeding parameter includes a flow rate of the first concentrate in the first line.

9. The apparatus of claim 1, wherein the feeding parameter includes a ratio between a flow of the first concentrate in the first line and a fluid flow in the main line.

10. The apparatus of claim 1, wherein the feeding parameter includes a ratio between a flow of the first concentrate in the first line and a flow of the medical fluid in the main line downstream of both the first and the second mixing points.

11. The apparatus of claim 1, wherein the concentration sensor is positioned and arranged for the use of the first and the second concentrates for on-line preparation of the medical fluid.

\* \* \* \* \*